United States Patent
Kaneda

(10) Patent No.: US 9,506,849 B2
(45) Date of Patent: Nov. 29, 2016

(54) MATERIAL TESTING MACHINE

(71) Applicant: SHIMADZU CORPORATION, Kyoto-shi, Kyoto (JP)

(72) Inventor: Masaki Kaneda, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 14/706,194

(22) Filed: May 7, 2015

(65) Prior Publication Data
US 2015/0330882 A1    Nov. 19, 2015

(30) Foreign Application Priority Data

May 13, 2014   (JP) .................. 2014-099496

(51) Int. Cl.
G01N 3/04        (2006.01)
G01N 3/08        (2006.01)

(52) U.S. Cl.
CPC .... *G01N 3/04* (2013.01); *G01N 3/08* (2013.01); *G01N 2203/0254* (2013.01); *G01N 2203/0447* (2013.01)

(58) Field of Classification Search
CPC ........................................................ G01N 3/04
USPC ............................................................ 73/831
See application file for complete search history.

(56) References Cited

U.S. PATENT DOCUMENTS

| 6,860,156 B1 | 3/2005 | Cavallaro et al. |
| 7,500,401 B2 * | 3/2009 | Tsai ............... G01N 3/04 73/859 |
| 8,671,771 B2 * | 3/2014 | Hanabusa ......... G01N 3/04 73/826 |
| 2015/0101418 A1 | 4/2015 | Campbell et al. |

FOREIGN PATENT DOCUMENTS

| FR | 2 579 327 A1 | 3/1985 |
| JP | 2012-032218 A | 2/2012 |
| WO | 2013/158774 A1 | 10/2013 |

* cited by examiner

*Primary Examiner* — Lisa Caputo
*Assistant Examiner* — Octavia Hollington
(74) *Attorney, Agent, or Firm* — Westerman, Hattori, Daniels & Adrian, LLP

(57) ABSTRACT

When a crosshead descends after a specimen is loaded, pins attached to link members contact seat surfaces formed on seat members, and then contact side walls of the seat surfaces. As the crosshead descends further, the pins contacting the seat surfaces press the seat members 31. This pressing force moves a pair of first slide members away from each other as guided by a first rail, and moves a pair of second slide members away from each other as guided by a second rail 24. Consequently, tension loads in biaxial directions perpendicular to each other are applied to the specimen gripped by four chucks 25.

6 Claims, 10 Drawing Sheets

MATERIAL TESTING MACHINE

BACKGROUND OF THE INVENTION

1. Field of the Invention

This invention relates to a material testing machine for testing specimens by applying thereto tensile forces in biaxial directions perpendicular to each other.

2. Description of the Prior Art

Such material test is also called a biaxial tensile test, which is conducted when measuring the strength of a metal plate, for example. Japanese Unexamined Patent Publication No. 2012-32218 discloses, as such a material testing machine, a biaxial tensile testing machine which includes a pair of specimen chucks movably arranged on each of two rails extending in directions perpendicular to each other.

FIG. 11 is a perspective view showing a biaxial tension mechanism for applying testing forces to a specimen 100 in such conventional material testing machine.

The biaxial tension mechanism in this material testing machine includes a first rail 91 and a second rail 92 arranged on the surface of a base plate 90 to extend in directions perpendicular to each other. The first rail 91 has a pair of first moving members 93 slidably arranged thereon. These first moving members 93, by being guided by the first rail 91, are movable toward and away from each other along the first rail 91. Each of these first moving members 93 has a chuck 95 for gripping the specimen 100. On the other hand, the second rail 92 has a pair of second moving members 94 (only one of them appearing in FIG. 11) slidably arranged thereon. These second moving members 94, by being guided by the second rail 92, are movable toward and away from each other along the second rail 92. Each of these second moving members 94 has a chuck 96 for gripping the specimen 100. The base plate 90 which supports the first rail 91 and second rail 92 is disposed on a base block in a material testing machine body.

This biaxial tension mechanism includes a load member 80 connected to a crosshead in the material testing machine, for receiving a load applied from the crosshead. The pair of first moving members 93 are connected to the load member 80 by link members 83 each formed of a link 81 and a link 82. The link 81 forming part of each link member 83 is rockably connected to the first moving member 93 by a pivot 97. The link 82 forming part of each link member 83 is rockably connected to the load member 80 by a pivot 85. The pair of second moving members 94 are connected to the load member 80 by link members 84. One end of each link member 84 is rockably connected to the second moving member 94 by a pivot 98. The other end of each link member 84 is rockably connected to the load member 80 by a pivot 86.

With the biaxial tension mechanism in this material testing machine, when the load member 80 is pressed in a state of the specimen 100 gripped by the two pairs of chucks 95 and 96, the pair of first moving members 93 are moved, by action of the link members 83, away from each other along the first rail 91, and the pair of second moving members 94 are moved, by action of the link members 84, away from each other along the second rail 92. Consequently, tension loads in the biaxial directions perpendicular to each other are applied to the specimen 100 gripped by the two pairs of chucks 95 and 96.

As noted above, the biaxial tension mechanism of the material testing machine described in Japanese Unexamined Patent Publication No. 2012-32218 has a construction in which the pair of first moving members 93 and the load member 80 are connected by the link members 83, and the pair of second moving members 94 and the load member 80 are connected by the link members 84. With this construction, when placing the specimen 100 in a state gripped by the chucks 95 and 96 or detaching the specimen 100, the operator needs to put in their hands through gaps between the link members 83 and 84 to carry out an attaching or detaching operation, which constitutes bad working efficiency. Particularly when a tool such as a spanner needs to be used in attaching or detaching the specimen 100 to/from the chucks 95 and 96, there arises a problem of requiring a very long time for attaching or detaching the specimen 100, which is due to interference between the tool and the link members 83 and 84.

SUMMARY OF THE INVENTION

The object of this invention, therefore, is to provide a material testing machine which allows a specimen to be attached and detached easily to/from chucks, which material testing machine tests the specimen by applying thereto tensile forces in biaxial directions perpendicular to each other.

The above object is fulfilled, according to this invention, by a material testing machine comprising a pair of first moving members each having a chuck for gripping a specimen, the first moving members being movable toward and away from each other along a first axis by being guided by a guide member; a pair of second moving members each having a chuck for gripping the specimen, the second moving members being movable toward and away from each other along a second axis by being guided by a guide member; a load member for receiving a load applied by a loading mechanism; and four link members for connecting the pair of first moving members and the pair of second moving members to the load member, respectively; the load applied to the load member being transmitted through the four link members to the pair of first moving members and the pair of second moving members, thereby synchronously to move the pair of first moving members away from each other along the first axis, and to move the pair of second moving members away from each other along the second axis; wherein either the first moving members and the second moving members or the link members have seat surfaces formed thereon, while the other have contact portions formed thereon and shaped to correspond to the seat surfaces; and the seat surfaces and the contact portions are movable into contact with each other, respectively, thereby to connect the pair of first moving members and the pair of second moving members to the load member through the four link members.

According to such material testing machine, in the material testing machine which conducts a test by applying to a specimen tensile forces in biaxial directions perpendicular to each other, the seat surfaces and the contact portions are moved away from each other, whereby the unit having the chucks and the first and second moving members and the unit having the load member and link members can be separated easily. The specimen can therefore be easily attached to and detached from the chucks.

In one preferred embodiment, the contact portions comprise pins for contacting the seat surfaces, and each of the seat surfaces has an opening area formed in at least one of directions other than a direction of load transfer between the pin and the seat surface.

In another preferred embodiment, the seat surfaces are formed on the first moving members and the second moving members, while the pins are arranged on the link members.

According to such material testing machine, the first moving members and the second moving members can be moved by applying pressing forces between the pins and the seat surfaces. By moving the pins away from the seat surfaces through the opening areas formed around the seat surfaces, the unit having the chucks and the first and second moving members and the unit having the load member and link members can be separated easily. The specimen can therefore be easily attached to and detached from the chucks.

In a further preferred embodiment, the four link members are rockably attached to the load member connected to a crosshead, and the guide member for guiding the first moving members and the guide member for guiding the second moving members are fixed on a base portion disposed on a base block.

According to such material testing machine, tensile forces in the biaxial directions perpendicular to each other can be applied to the specimen by using the movement of the cross-head relative to the base block.

Other features and advantages of the invention will be apparent from the following detailed description of the embodiments of the invention.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

Figure 1:
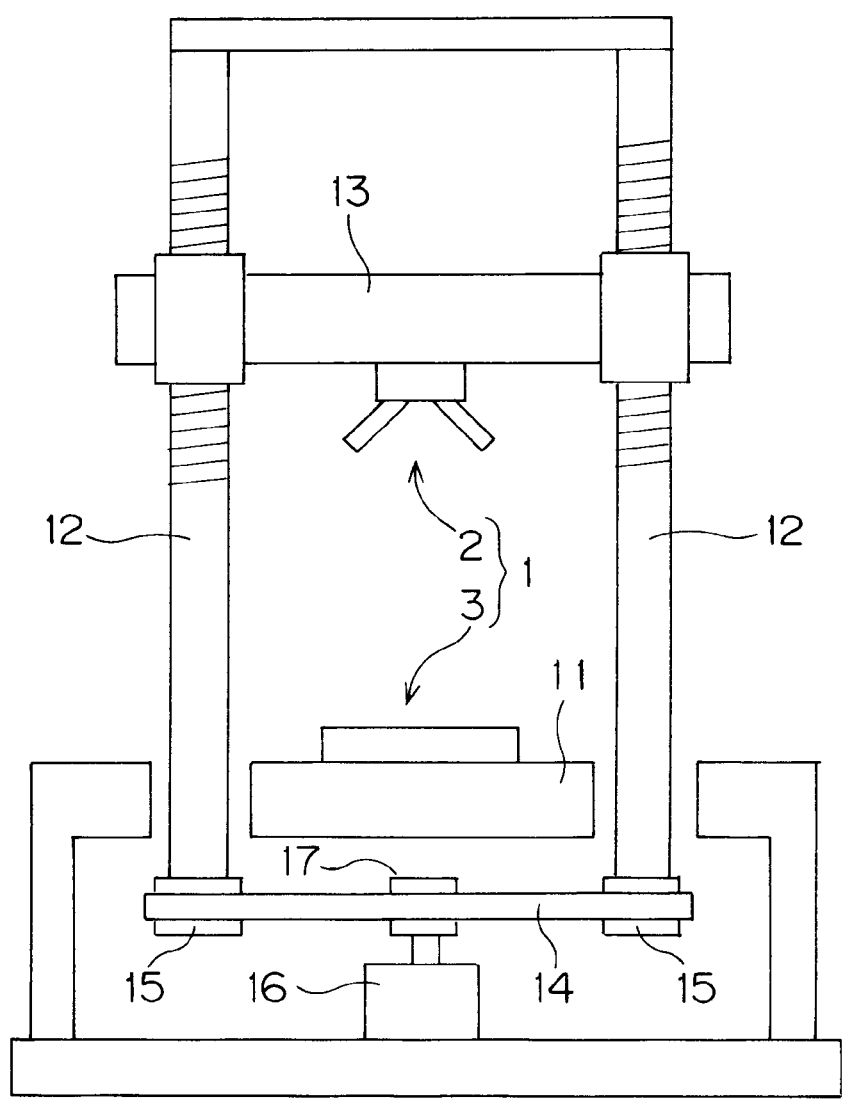
FIG. 1 is a schematic view of a material testing machine according to this invention.

An embodiment of this invention will be described hereinafter with reference to the drawings. FIG. 1 is a schematic view of a material testing machine according to this invention.

This material testing machine includes a base block 11, a pair of right and left screw poles 12 erected on the base block 11, and a crosshead 13 having nuts meshed with the right and left screw poles 12 and movable up and down relative to the screw poles 12. The crosshead 13 has, attached thereto, an upper unit 2 of a biaxial tension mechanism 1 described hereinafter. The base block 11 has, attached thereto, a lower unit 3 of the biaxial tension mechanism 1 described hereinafter.

The pair of screw poles 12 have, mounted on bottom ends thereof, respectively, synchronization pulleys 15 engaged with a synchronous belt 14. This synchronous belt 14 engages also a synchronization pulley 17 rotatable by drive of a motor 16. The pair of screw poles 12 are therefore synchronously rotatable by drive of the motor 16. With synchronous rotation of the pair of screw poles 12, the crosshead 13 moves up and down axially of the screw poles 12.

Figure 2:
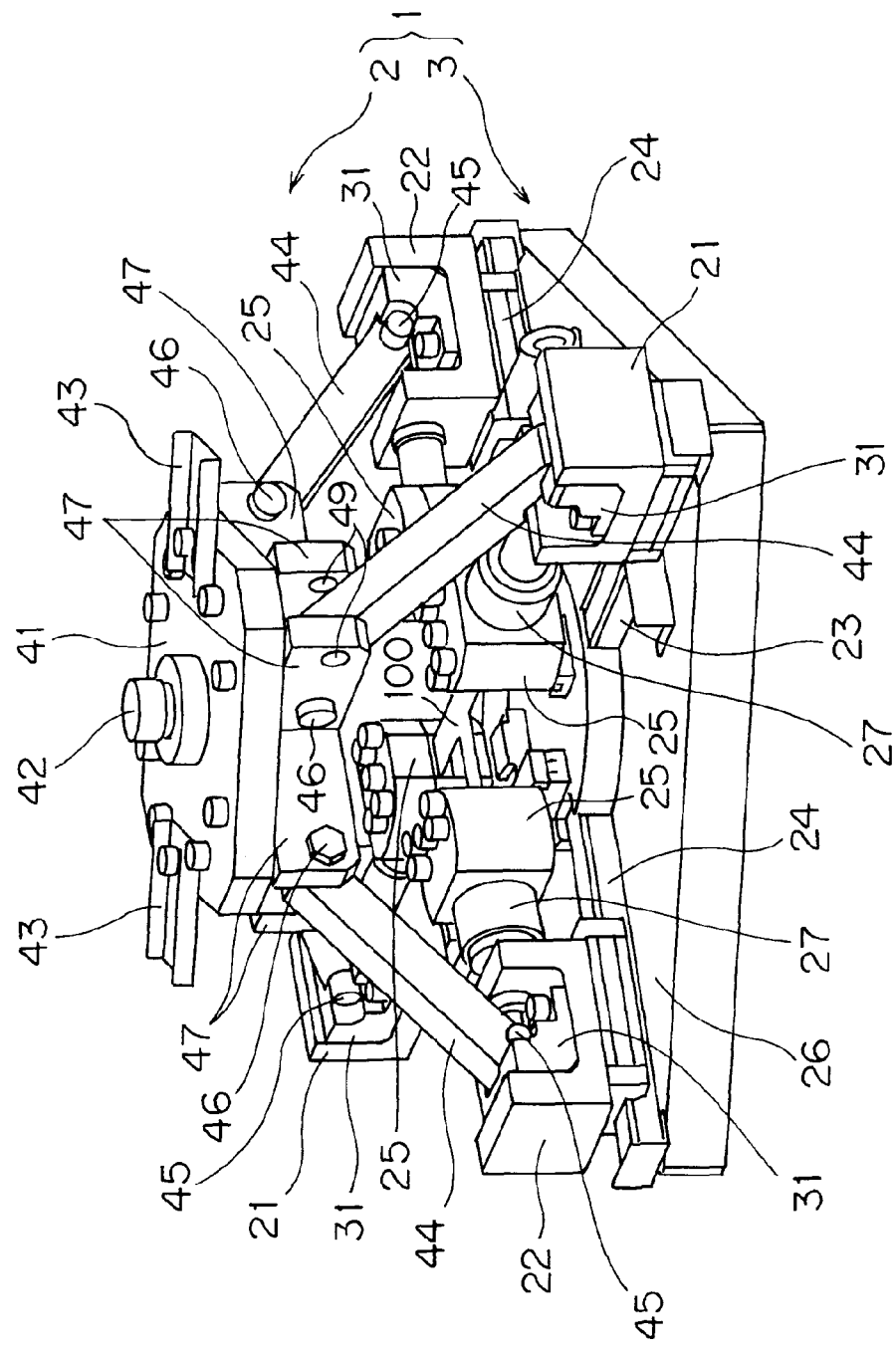
FIG. 2 is a perspective view of a biaxial tension mechanism.

FIG. 2 is a perspective view of the biaxial tension mechanism 1 noted above. FIG. 2 shows a state of the upper unit 2 and lower unit 3 of the biaxial tension mechanism 1 connected to each other.

This biaxial tension mechanism 1 includes a first rail 23 and a second rail 24 arranged on the surface of a base portion 26 to extend in directions perpendicular to each other. The base portion 26 which supports the first rail 23 and second rail 24 is disposed on the base block 11 in a material testing machine body shown in FIG. 1.

The first rail 23 has a pair of first slide members 21 slidably arranged thereon. These first slide members 21, by being guided by the first rail 23, are movable toward and away from each other along a first axis parallel to the first rail 23. One of these first slide members 21 is connected through a load cell 27 to a chuck 25 for gripping a specimen 100. The other of the first slide members 21 is connected directly to a chuck 25. Each of the first slide members 21 holds a seat member 31 having seat surfaces 29 formed thereon as described hereinafter. The first slide members 21 and seat members 31 constitute the first moving members in this invention.

On the other hand, the second rail 24 has a pair of second slide members 22 slidably arranged thereon. These second slide members 22, by being guided by the second rail 24, are movable toward and away from each other along a second axis parallel to the second rail 24. One of these second slide members 22 is connected through a load cell 27 to a chuck 25. The other of the second slide members 22 is connected directly to a chuck 25. Each of the second slide members 22 holds a seat member 31, as does each first slide member 21. The second slide members 22 and seat members 31 constitute the second moving members in this invention.

The first and second rails 23 and 24, first and second slide members 21 and 22, seat members 31, load cells 27 and chucks 25 arranged on the base portion 26 constitute the lower unit 3 of the biaxial tension mechanism 1.

The biaxial tension mechanism 1 includes a support 41 connected by a connecting member 42 to the crosshead 13 in the material testing machine shown in FIG. 1. A load is applied from the crosshead 13 to the support 41 at the time of a biaxial tensile test described hereinafter. The support 41 has, attached thereto, a pair of lift members 43 used when the biaxial tension mechanism 1 or its upper unit 2 is transported by a forklift or the like. This support 41 acts as the load member according to this invention, to which a load is applied by the crosshead 13 acting as the loading mechanism.

The support 41 has, attached thereto, four link members 44 each pinched between a pair of joint members 47. These link members 44 are attached to be rockable about pivots 46 relative to the joint members 47. The support 41 and the four link members 44 attached to the support 41 by the joint members 47 and pivots 46 constitute the upper unit 2 of the biaxial tension mechanism 1.

Of the joint members 47 supporting the four link members 44, the joint members 47 corresponding to the first slide members 21 have, formed therein, bores 49 separately from the bores for receiving the pivots 46. These bores 49 are used when changing a ratio between testing forces applied to the specimen 100 in the directions perpendicular to each other. In this case, two of the four link members 44 will be rock about the pivots 46 attached to the bores 49.

Figure 3:
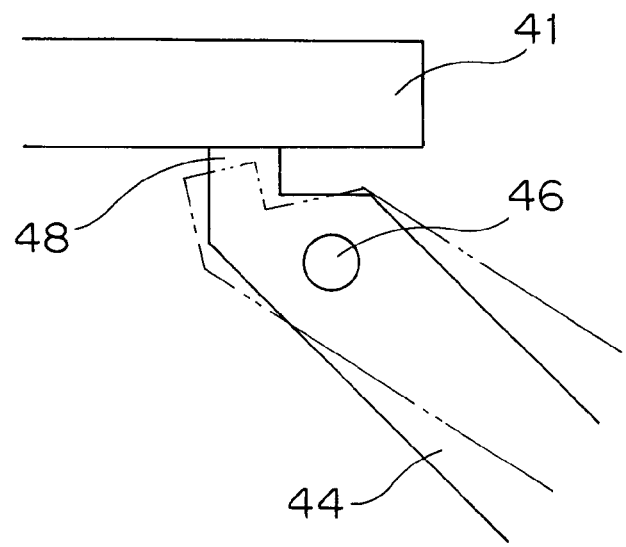
FIG. 3 is an explanatory view showing a state of a link member attached to a support.

FIG. 3 is an explanatory view showing a state of a link member 44 attached to the support 41.

As shown in FIGS. 2 and 3, each link member 44 is attached by the joint members 47 and pivot 46 to be rockable relative to the support 41. With a projection 48 formed at the upper end of each link member 44 contacting a lower surface of the support 41, rocking of the link member 44 is restricted to a position shown in a solid line in FIG. 3. Consequently, when the upper unit 2 and lower unit 3 are separated as described hereinafter, each link member 44 can be prevented from hanging down. The projection 48 formed on each link member 44 for contacting the lower surface of the support 41 acts as a restricting member for restricting a rocking range of each link member 44.

Figure 4:
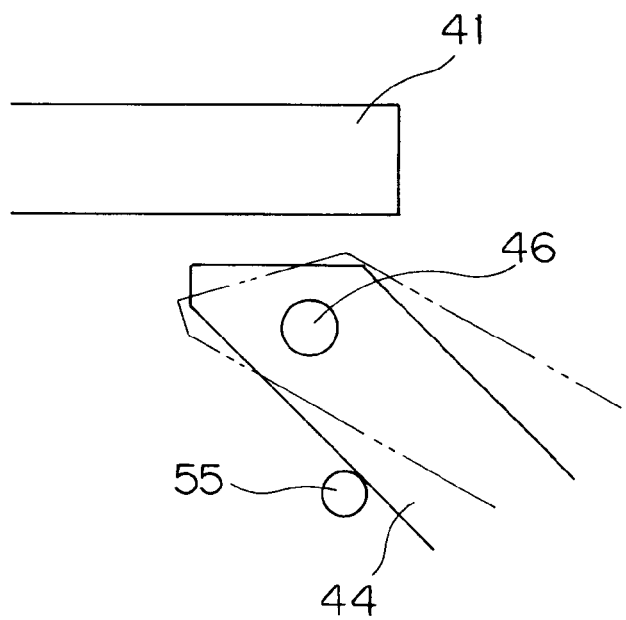
FIG. 4 is an explanatory view showing a state of a link member attached to a support according to another embodiment.

FIG. 4 is an explanatory view showing a state of a link member 44 attached to the support 41 according to another embodiment.

This embodiment omits the projection 48 formed at the upper end of each link member 44 in the embodiment described above, and provides a restricting pin 55 for restricting rocking of the link member 44 to a position shown in a solid line in FIG. 4. In this embodiment also, when the upper unit 2 and lower unit 3 are separated, each link member 44 can be prevented from hanging down. This restricting pin 55 acts as the restricting member for restricting the rocking range of each link member 44.

Referring to FIG. 2 again, each link member 44 has pins 45 arranged adjacent a lower end thereof. When the upper unit 2 and lower unit 3 are connected as described hereinafter, the pins 45 will contact the seat surfaces 29 formed on each seat member 31.

Next, an operation for performing a biaxial tensile test on the specimen 100 using this biaxial tension mechanism 1 will be described.

As noted hereinbefore, the upper unit 2 of the biaxial tension mechanism 1 is attached to the crosshead 13 of the material testing machine. The lower unit 3 of the biaxial tension mechanism 1 is attached to the base block 11 of the material testing machine. In this state, the upper unit 2 is not located over the lower unit 3 of the biaxial tension mechanism 1, and therefore an area over each chuck 25 in the lower unit 3 is open. The specimen 100 can therefore be loaded on these chucks 25 easily. Even if it is necessary to use a tool such as a spanner at the time of loading the specimen 100, the operation can be carried out easily. In this state, in the upper unit 2 of the biaxial tension mechanism 1, as shown in FIG. 3, the projection 48 formed at the upper end of each link member 44 is in contact with the lower surface of the support 41, whereby each link member 44 is located in the position shown in the solid line in FIG. 3.

When the specimen 100 has been loaded on the chucks 25 and a biaxial tensile test is carried out on the specimen 100, the crosshead 13 is lowered along with the upper unit 2 of the biaxial tension mechanism 1 by drive of the motor 16 shown in FIG. 1. This moves the pins 45 in the upper unit 2 into contact with the seat members 31 in the lower unit 3.

Figure 5:
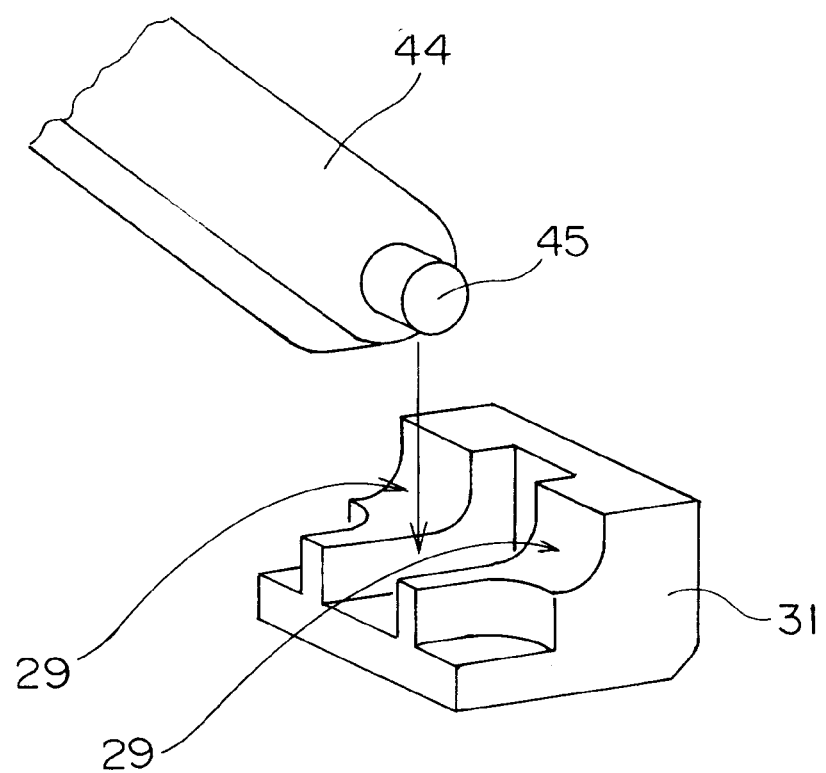
FIG. 5 is a perspective view showing a state of pins and a seat member coming into contact.
Figure 6:
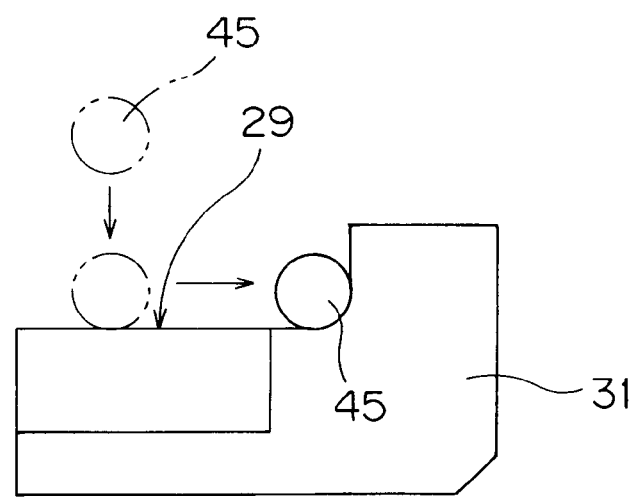
FIG. 6 is a schematic side view showing a state of the pins and the seat member coming into contact.

FIG. 5 is a perspective view showing a state of pins 45 and a seat member 31 coming into contact. FIG. 6 is schematic side view of this state.

Each of the seat members 31 held by the first and second slide members 21 and 22 in the lower unit 3 has the seat surfaces 29 formed thereon for contacting the pins 45 disposed on the link member 44 in the upper unit 2. The seat surfaces 29 and pins 45 have corresponding shapes.

When, after the specimen 100 is loaded, the crosshead 13 descends from the state shown in FIG. 1, the pins 45 attached to each link member 44 move into contact with the seat surfaces 29 formed on the seat member 31 as shown in FIGS. 5 and 6. When the crosshead 13 descends further from this state, the pins 45 slide on the seat surfaces 29 and contact side walls of the seat surfaces 29 as shown in solid lines in FIG. 6. At this time, the link member 44 rocks about the pivot 46 as shown in a phantom line in FIG. 3.

When the crosshead 13 descends further, the pins 45 in contact with the seat surfaces 29 press the seat member 31. Such pressing forces move the pair of first slide members 21 away from each other as guided by the first rail 23, and the pair of second slide members 22 away from each other as guided by the second rail 24. At this time, outer circumferential surfaces of the pins 45 and the seat surfaces 29 of each seat member 31 make sliding movement. Consequently, tension loads are applied in the biaxial directions perpendicular to each other, to the specimen 100 gripped by the four chucks 25. Values of the tension loads, i.e. testing forces, occurring at this time are measured by the pair of load cells 27.

When the biaxial tensile test has been completed, the crosshead 13 is raised again along with the upper unit 2 of the biaxial tension mechanism 1. When the upper unit 2 moves up, each link member 44 will rock under its own weight, which moves the pins 45 away from the side walls of the seat surfaces 29. The seat surfaces 29 formed on each seat member 31 are open in other areas than in the direction in which the pins 45 make contact and apply the load. Thus, as the crosshead 13 moves further upward, the ascent of the link member 44 will result in the pins 45 separating from the seat surfaces 29. At this time, as shown in the solid line in FIG. 3, the rocking of each link member 44 will stop in the position where the projection 48 formed at the upper end of the link member 44 contacts the lower surface of the support 41. Thus, the rocking of the link member 44 can be maintained within a fixed range, thereby to prevent the link member 44 from hanging down.

When the crosshead 13 is again placed in a raised position as shown in FIG. 1, the specimen 100 will be removed from the chucks 25. At this time also, the area over each chuck 25 in the lower unit 3 of the biaxial tension mechanism 1 is open, and therefore the specimen 100 can be removed from the chucks 25 easily.

Figure 7:
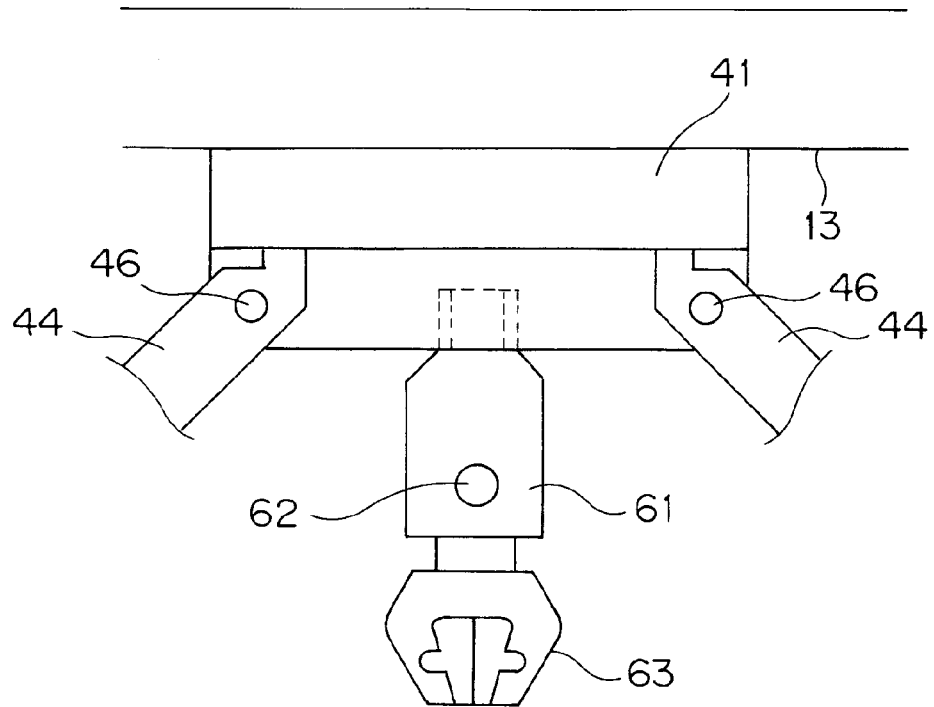
FIG. 7 is an explanatory view schematically showing a state of carrying out an ordinary tensile test with this material testing machine.
Figure 7:
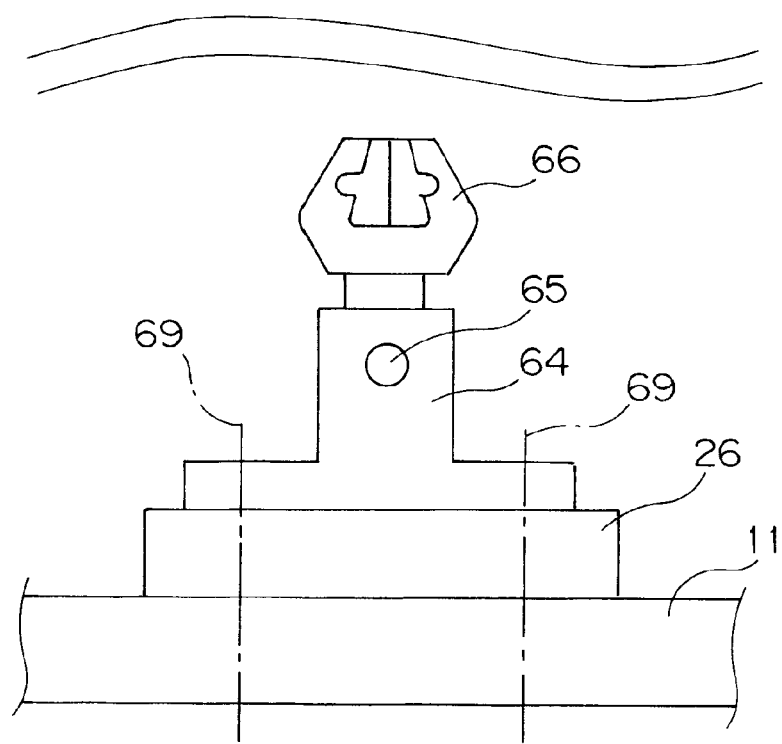

This material testing machine has such a construction that enables not only the biaxial tensile test but an ordinary material test. FIG. 7 is an explanatory view schematically showing a state of carrying out an ordinary tensile test with this material testing machine.

As shown in FIG. 7, an upper adapter 61 for attaching an upper gripper 63 is detachably attachable by a screw mechanism to the support 41 connected to the crosshead 13. The upper gripper 63 is attached to the upper adapter 61 using pins 62. On the other hand, a lower adapter 64 for attaching a lower gripper 66 is detachably attachable by screws 69 to the base portion 26 and base block 11. As shown in this figure, the upper adapter 61 for attaching the upper gripper 63 is attachable to the crosshead 13 through the support 41, and the lower adapter 64 for attaching the lower gripper 66 is attachable to the base block 11 through the base portion 26. This construction enables the material testing machine to perform both the ordinary material test and the biaxial tensile test.

In the foregoing embodiment, as shown in FIGS. 5 and 6, each seat member 31 has the seat surfaces 29 which are open in all directions other than the direction in which the pins 45 make contact and apply the load. However, the seat surfaces 29 of each seat member 31 are not limited to such shape.

Figure 8:
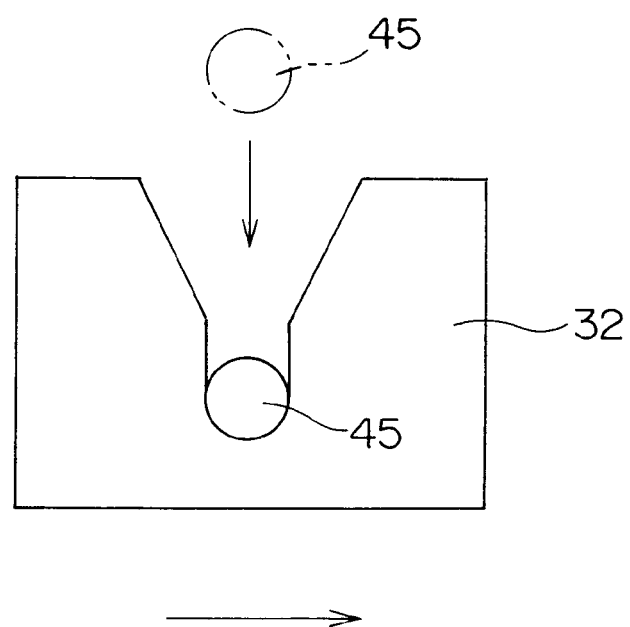
FIG. 8 is a schematic side view showing, along with a pin, a seat member according to a second embodiment.

FIG. 8 is a schematic side view showing, along with a pin 45, a seat member 32 according to a second embodiment.

This seat member 32 has a configuration having a V-shaped opening formed in an upper part thereof, and a U-shaped opening formed in a lower part and corresponding to the shape of the pins 45. This seat member 32 is shaped to be open upward, which is a direction other than the direction of load application between the pins 45 and the seat member 32. Also when such seat members 32 are used, the upper unit 2 and lower unit 3 of the biaxial tension mechanism 1 are easily separable by moving the pins 45 away from the seat members 32. It is also possible to connect the upper unit 2 and lower unit 3 for applying the testing force to the specimen 100.

Figure 9:
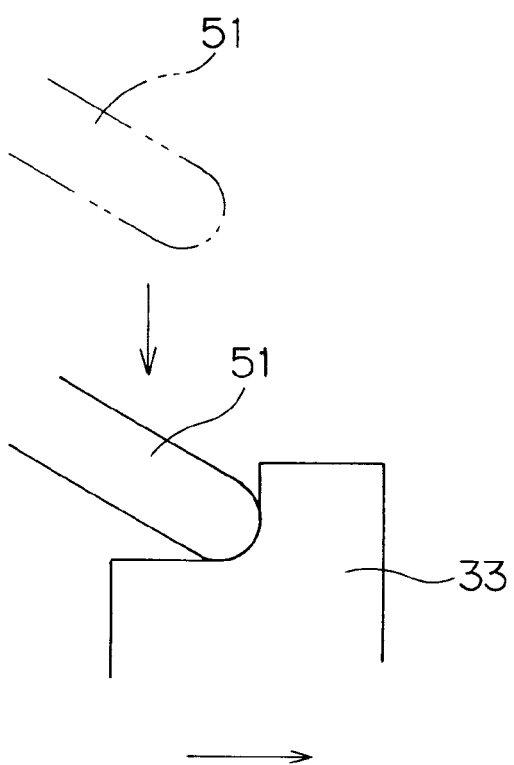
FIG. 9 is a schematic side view showing, along with a link member, a seat member according to a third embodiment.

FIG. 9 is a schematic side view showing, along with a link member 51, a seat member 33 according to a third embodiment.

This seat member 33 has a similar shape to the seat member 31 in the first embodiment. On the other hand, the link member 51 in this embodiment has a forward end thereof acting as a contact portion shaped to correspond to a seat surface of the seat member 33. Also when such seat members 33 and link members 51 are used, the upper unit 2 and lower unit 3 of the biaxial tension mechanism 1 are easily separable by moving the link members 51 away from the seat members 33. It is also possible to apply the testing force to the specimen 100 with the contact portions at the forward ends of the link members 51 pressing the seat surfaces of the seat members 33.

Figure 10:
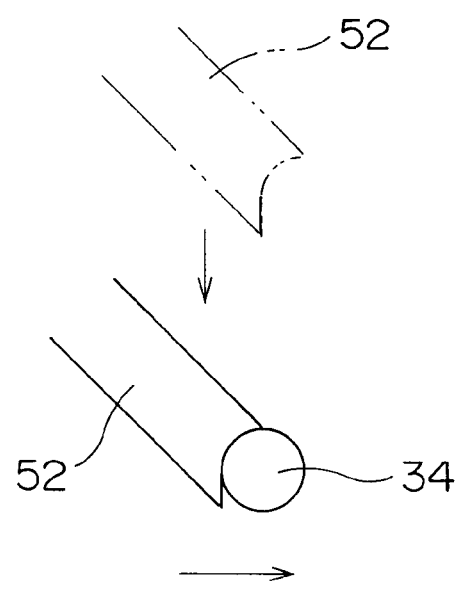
FIG. 10 is a schematic side view showing a pin with a link member.
Figure 11:
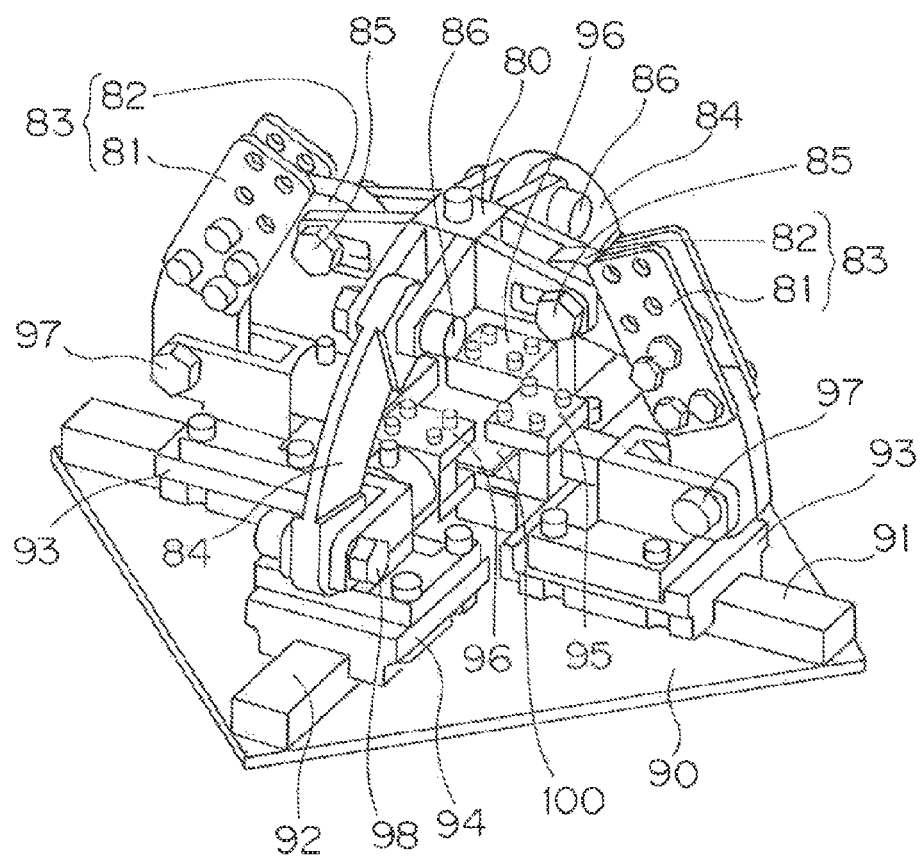
FIG. 11 is a perspective view showing a biaxial tension mechanism for applying testing forces to a specimen in a conventional material testing machine.

FIG. 10 is a schematic side view showing, along with a link member 52, a pin 34 used in place of each of the seat members 31, 32 and 33 described hereinbefore.

In this embodiment, the pin 34 used in place of each of the seat members 31, 32 and 33 described hereinbefore. Such pins 34 are supported by the first slide members 21 and second slide members 22. On the other hand, in this embodiment, each link member 52 has a seat surface formed at a forward end thereof and shaped to correspond to each pin 34. Also when such pins 34 and link members 52 are used, the upper unit 2 and lower unit 3 of the biaxial tension mechanism 1 are easily separable by moving the link members 52 away from the pins 34. It is also possible to apply the testing force to the specimen 100 with the seat surfaces at the forward ends of the link members 52 pressing the pins 34.

As described above, the seat surfaces and contact portions in this invention have a characteristic construction for contacting each other to transmit forces in a situation of performing a material test. In a different situation, the seat surfaces and contact portions can easily be moved out of contact and separated from each other.

The foregoing embodiments have been described taking the case of performing a biaxial tensile test, for example, which applies to the specimen 100 tensile forces in the directions perpendicular to each other by using the first rail 23 and second rail 24 arranged on the surface of the base portion 26 to expend perpendicular to each other, and moving the pair of first slide members 21 and the pair of second slide members 22 in the directions perpendicular to each other. This invention may be applied to a material testing machine for performing a triaxial tensile test, which machine includes the first rail 23 and second rail 24 arranged to cross each other, and further includes a third rail arranged to cross the first and second rails. Tensile forces are applied to the specimen tensile forces in triaxial directions by sliding third slide members connected to chucks along this third rail. It is also possible to apply this invention to a machine for performing a material test by applying to the specimen tensile forces in quadraxial or more directions.

This invention may be embodied in other specific forms without departing from the spirit or essential attributes thereof and, accordingly, reference should be made to the appended claims, rather than to the foregoing specification, as indicating the scope of the invention.

This application claims priority benefit under 35 U.S.C. Section 119 of Japanese Patent Application No. 2014-099496 filed in the Japanese Patent Office on May 13, 2014, the entire disclosure of which is incorporated herein by reference.

What is claimed is:

1. A material testing machine comprising:
a lower unit, the lower unit comprising:
a pair of first moving members each having a chuck for gripping a specimen, the first moving members being movable toward and away from each other along a first axis by being guided by a guide member;
a pair of second moving members each having a chuck for gripping the specimen, the second moving members being movable toward and away from each other along a second axis by being guided by a guide member;
an upper unit, separable from the lower unit, the upper unit comprising:
a load member for receiving a load applied by a loading mechanism; and
four link members for connecting the pair of first moving members and the pair of second moving members to the load member, respectively;
the load applied to the load member being transmitted through the four link members to the pair of first moving members and the pair of second moving members, thereby synchronously to move the pair of first moving members away from each other along the first axis, and to move the pair of second moving members away from each other along the second axis;
wherein either the first moving members and the second moving members or the link members have seat surfaces formed thereon, while the other have contact portions formed thereon and shaped to correspond to the seat surfaces; and
the seat surfaces and the contact portions are movable into contact with each other, respectively, thereby to connect the pair of first moving members and the pair of second moving members to the load member through the four link members.

2. The material testing machine according to claim 1, wherein:
the contact portions comprise pins for contacting the seat surfaces; and each of the seat surfaces has an opening area formed in at least one of directions other than a direction of load transfer between the pin and the seat surface.

3. The material testing machine according to claim 2, wherein the seat surfaces are formed on the first moving members and the second moving members, while the pins are arranged on the link members.

4. The material testing machine according to claim 1, wherein:
- the four link members are rockably attached to the load member connected to a crosshead; and
- the guide member for guiding the first moving members and the guide member for guiding the second moving members are fixed on a base portion disposed on a base block.

5. The material testing machine according to claim 4, comprising restricting members each for restricting a rocking range of one of the link members.

6. The material testing machine according to claim 4, comprising:
- an upper adapter detachably attachable to the load member for attaching an upper gripper; and
- a lower adapter detachably attachable to the base portion for attaching a lower gripper.

* * * * *